United States Patent [19]

Gartner

[11] Patent Number: 4,526,751
[45] Date of Patent: Jul. 2, 1985

[54] GERMICIDAL SOLUTIONS EFFECTIVE FOR SOLID SURFACE DISINFECTION

[76] Inventor: William J. Gartner, 153 Williamsburg Dr., Bartlett, Ill. 60103

[21] Appl. No.: 559,898

[22] Filed: Dec. 9, 1983

[51] Int. Cl.$^3$ ..................... A61K 31/79; A61K 33/18
[52] U.S. Cl. ........................................ 422/37; 424/80; 424/150
[58] Field of Search ............ 210/501; 252/106, 187.1; 422/37; 424/80, 150

[56] References Cited

U.S. PATENT DOCUMENTS

| | | | |
|---|---|---|---|
| 2,706,701 | 4/1955 | Beller et al. | 424/150 |
| 2,754,245 | 7/1956 | Hosmer | 424/150 |
| 2,868,686 | 1/1959 | Shelanski et al. | 424/150 |
| 3,028,300 | 4/1962 | Cantor et al. | 424/80 |
| 3,898,326 | 8/1975 | Cantor et al. | 424/80 |
| 4,131,556 | 12/1978 | Klopotek et al. | 424/150 |
| 4,235,884 | 11/1980 | Salkin | 424/150 |

FOREIGN PATENT DOCUMENTS 1475695 6/1977 United Kingdom .

*Primary Examiner*—Ivars Cintins
*Attorney, Agent, or Firm*—Robert E. Wagner; Ralph R. Rath; Sidney Wallenstein

[57] ABSTRACT

A germicidal solution effective for disinfection of solid surfaces to destroy or to inactivate bacteria, microorganisms, protozoa, molds and viruses and the like contaminating said surfaces which comprises a polyvinylpyrrolide-aqueous solution of elemental iodine, a water-soluble iodide, and potassium bromide, said solution containing a sufficiently high concentration of elemental iodine to effect said destruction or inactivation.

15 Claims, No Drawings

GERMICIDAL SOLUTIONS EFFECTIVE FOR SOLID SURFACE DISINFECTION

BACKGROUND OF THE INVENTION

Numerous germicidal or disinfectant solutions are known to the art for disinfection of solid surfaces of various types, including hard surfaces such as metals, glass, ceramics, wooden, terrazo and composition flooring, and numerous other hard surfaces; as well as for disinfection of soft surfaces such as, for example, the human skin, tissues, and the like, for swabbing the skin of a patient prior to surgery, the washing of a surgeon's or technician's hands, and in related and unrelated environments. They function with various degrees of efficacy, but their purpose and objective is to effect the killing or inactivation of surface bacteria, microorganisms, protozoa, molds and viruses of many and numerous types.

My present invention is concerned with that type of germicidal solution, which depends mainly or essentially on iodine for its disinfective utility. Numbers of such germicidal solutions are known to, and have been proposed by, the art; and some are in current active use with, generally speaking, effective results. One of such commercially available iodine-based disinfectant additives is known under the designation of Iodophors. Another of such iodine-based disinfecting solutions, which is similar to the Iodophors in only certain of its characteristics and which is in present relatively widespread use, is that sold under the designation or trademark "Betadine" (Purdue-Fredericks). This is a Povidone-Iodine product, Povidone being a common designation for polyvinylpyrrolidone (which is also commonly called PVP). The manufacture of PVP-Iodine products involves procedures which, generally speaking, are time-consuming and difficult to control and, therefore, cause such products to be expensive, particularly where such products have a relatively high concentration of iodine, which retains its solubility in the solution in which it is prepared and sold. Iodine is soluble in water in the amount of 300 mg. per liter of water at 25° C. (Handbook of Chemistry and Physics). A typical or illustrative "Betadine" type of product contains an approximately 10% mixture of PVP and iodine, with the proportions of PVP and iodine being somewhat variable. The PVP appears to function as a chelating agent and surfactant; and it is essentially the agent which permits the relatively high concentration of iodine to remain in solution. By high concentrations of iodine, in products of the "Betadine" type, I mean concentrations in the general range of about 1% or somewhat above 1% by weight, in solution in the aqueous PVP. In the production of the "Betadine" products, it is understood that it appears to be required that the PVP be dry-ground with sublimated or resublimated crystalline iodine until said iodine is completely or essentially completely dispersed. The resulting mixture or dispersion must then be mixed in a high-speed shear-type mixer with hot water to arrive at the 10% PVP-Iodine level. The final PVP-Iodine compositions commonly or generally contain in the approximate range of about 1% iodine in solution.

SUMMARY OF THE PRESENT INVENTION

In accordance with my present invention, an interhalogen, or mixture of halogen compounds, is preferably initially prepared and is then admixed with a water solution (or colloidal water solution, said terms being used interchangeably) of the PVP, preferably over a short period of time, and then diluted to the desired concentration of the iodine. The interhalogen admixture comprises a mixture, in water, of elemental iodine and water-soluble salts of iodine and potassium bromide. The water-soluble salts of iodine are advantageously ammonium iodide, sodium iodide or potassium iodide, or mixtures of any two or the three of them but, most advantageously, is potassium iodide. Essential to the achievement of the results of my invention is that the mixture of interhalogens contain potassium bromide. In short, mixtures of the water-soluble iodides can be used, but potassium iodide is especially satisfactory, and the presence of potassium bromide is essential. Since waters in various parts of this country vary appreciably in hardness, composition and in other respects, it is especially advantageous, particularly where the germicidal compositions of my present invention are used in hospital or similar environments, to use deionized (DI) water or distilled water in preparing the germicidal compositions.

Referring, now, to the proportions of the interhalogens which are used in the preparation of the germicidal solutions of my present invention, it may be stated that the proportions thereof are variable within reasonable limits, but the proportions are desirably such that the mixture of the sublimated or resublimated iodine, the water-soluble iodide and the potassium bromide be such as to form a clear, or substantially clear to the naked eye, solution such that the final solution, which contains the DI water and the PVP, is one in which the elemental iodine is present in solution in relatively high concentrations and remains in solution. Other ingredients can be incorporated as additives so as to adapt the compositions to particular application purposes of germicidal or disinfectant use as, for instance, scrub solutions, or gels for swabs, or for use as douches, or whatever the particular intended use of the germicidal compositions of my invention may be.

DETAILED DESCRIPTION OF THE PRESENT INVENTION

A detailed description of the invention is set forth below, including the best embodiment or embodiments of my invention of which I am presently aware. With due regard thereto, it will be understood that various changes may be made, in light of the guiding principles and teachings disclosed herein, without departing from the fundamental teachings of my invention as disclosed, and the Examples set out below are not to be construed as being in any way limitative of the full and true scope of my invention which are set out in the claims forming a part thereof.

Initial formulations of the interhalogen (IHS) solutions are made up, one containing 1% and the other containing 10%, by weight, in DI water, of a mixture of the aforestated sublimated or resublimated (elemental) iodine, potassium iodide and potassium bromide, in which the elemental iodine is in solution. Another set of examples is made up in which the PVP in selected proportions is dissolved or colloidally dispersed in DI water to provide solutions (or colloidal solutions which appear clear to the naked eye). Also, two different, alternative orders of mixing procedures may be employed, namely, (1) mixing together the dry intermixed interhalogen (I, KI and KBr) and the PVP and then adding the DI water, and (2) mixing together the DI water and the PVP and then adding the dry intermixed IHS. While various mixers or blenders can be used, it was found that, for small-scale use or for laboratory purposes, the well-known Osterizer blender is very satisfactory. It was used at its high-speed setting, and it also exhibits a good shearing action for the particular ingredients being admixed. A shearing action is particularly advantageous when bringing the PVP into solution in the DI water, regardless of whether the IHS has initially been added or not.

A particularly preferred embodiment for the IHS solution is as follows:

| COMPONENT A | WEIGHT (grams) | WEIGHT RATIO |
| --- | --- | --- |
| Iodine (elemental) | 220 | 11 |
| Potassium Iodide | 100 | 5 |
| Potassium Bromide | 20 | 1 |
| DI Water | 50 | 2.5 |

This is then admixed, in the proportions shown below as a part of the Component B, a germicidal solution representing one of the best embodiments of my invention of which I am presently aware.

| COMPONENT B | WEIGHT (grams) | WEIGHT RATIO |
| --- | --- | --- |
| PVP | 50 | 1 |
| DI Water | 500 | 10 |
| Component A | 50 | 1 |

The formulation of Component B provides a titrable or available Iodine level of 5%. This can be diluted, if desired, with DI water on a direct proportional basis to arrive at the desired concentration for the particular germicidal purpose required. The 5% Iodine concentrate, prepared as described above, can be utilized as the primary disinfectant in environments ranging from skin disinfecting agents, floor or other hard surface cleaners, or Udder washes for the dairy industry, and can be formulated by dilution or by the inclusion of additives for such uses as surgical scrubs, decubitus ulcer rinses, vaginal douches, etc., in which the titratable iodine content of the germicidal solutions or compositions is present in lower concentrations as, for example, about 1% or 2%, by weight. Germicidal solutions made in accordance with the present invention, generally speaking, exhibit superior germicidal characteristics at lower concentrations of available iodine and are simpler to manufacture and control.

The relative proportions of the elemental iodine, potassium iodide and potassium bromide are variable within relatively wide ranges, bearing in mind that the elemental iodine be and remain in solution in water and in the finished PVP aqueous solutions. In general, in the IHS composition, the weight ratios of the elemental iodine, the water-soluble iodides (specifically, potassium iodide) and the potassium bromide are such that the elemental iodine will constitute the major ingredient; the water-soluble iodide(s) or potassium iodide will be the second major ingredient; and the potassium bromide, although, as stated above, being an essential ingredient, will be present in the smallest amount. Again, generally speaking, the relationship, by weight, of the IHS component of the germicidal solutions of my invention, will generally be such that the elemental iodine will substantially exceed that of the potassium iodide or other water-soluble iodides; the potassium iodide or other water-soluble iodides will substantially exceed that of the potassium bromide; and the elemental iodide will exceed the sum of the amounts of the potassium iodide or other water-soluble iodides and the potassium bromide. The amount of DI water in which the IHS is dissolved will, of course, determine the concentration of the iodine in the aqueous solution, and in the PVP solutions of my present invention. With the ingredients constituting the following ranges of proportions by weight, in terms of grams, and, also, the weight ratios of IHS ingredients, the indicated ranges of proportions of water are advantageously used:

Elemental iodine: 200–230 g
KI: 90–120 g
KBr: 10–30 g
$H_2O$: 40–60 g

The relative proportions, by weight, of the PVP to the IHS of the germicidal compositions of my invention are variable between reasonable limits. Generally speaking, such relative proportions are desirably in the range of about 2:1 of the PVP to the IHS, to about 10:1 of the PVP to the IHS, as is indicated by the following additional illustrative germicidal compositions of my invention. The percentages listed are by weight.

| EXAMPLE | % PVP | % IHS* | MIX METHOD + | OBSERVATIONS |
| --- | --- | --- | --- | --- |
| A | 10 | 5 | 2 | Deep golden brown viscous liquid |
| B | 10 | 2 | 1 | Golden brown liquid |
| C | 10 | 1 | 2 | Golden brown liquid |
| D | 10 | 1 | 1 | Golden brown liquid |
| E | 2 | 1 | 2 | Golden brown liquid |

*The IHS composition utilized here represents one of the best embodiments of my invention of which I am presently aware, as indicated above, and corresponds to the ratio of the ingredients listed above under the heading "COMPONENT A".
+ Mix Method No. 1 - Mixing the PVP and IHS prior to the addition of the DI water.
Mix Method No. 2 - Mixing the PVP and DI water prior to the addition of the IHS.

As generally indicated above, in the preparation of an illustrative 5% titratable (available) Iodine in PVP aqueous solution involves simply placing 100 g DI water and 10 g PVP in an Osterizer blender, mixing at high speed until all of the PVP is in solution. A foam usually forms, which is allowed to subside on standing (commonly for about 30 minutes or so), after which 10 g (3.6 ml) of the IHS mixture is added and mixing is continued for a few minutes (usually 3 to 5 minutes).

Titrametric procedures are readily available to determine the amount of free or available iodine as a measure of the germicidal or antiseptic properties of the solutions. Thus, for instance, 2% IHS of the composition of Component A above in a DI-PVP solution gives a 1.066% iodine concentration.

The germicidal solutions of the present invention, as noted above, contain relatively high contents of elemental iodine in solution in the aqueous PVP solutions, advantageously strong solutions of elemental iodine, up to concentrated or substantially concentrated solutions, while maintaining the elemental iodine in solution. They are also desirably free or substantially free from adverse staining effects on the surfaces to which they are applied, and are readily removable by washing or rinsing in water.

The following additional tests were run to determine the germicidal effectiveness of "Bromadine"* 141 against *E.coli*, ATCC 11229; and *Ps.aeruginosa*, ATCC 15442.

* "Bromadine" was the trade designation or trademark given to the germicidal compositions prepared by the present invention. Specifically, "Bromadine 141" is the composition obtained utilizing Component B referred to above in the present specification.

Method:

AOAC Germicidal and Detergent Sanitizer Test (Chambers Modification of Weber and Black Method)

Conclusion:

At a 1:4 dilution, "Bromadine" 141 gave 99.999+ reduction against *E.coli* and *Ps.aeruginosa* in 30 seconds. At full strength, with a 5% organic load, "Bromadine" 141 gave 99.999+ reduction against *E.coli* and *Ps.aeruginosa*.

| TESTS | | | |
|---|---|---|---|
| Product | Exposure Time (seconds) | Count | % Reduction |
| Organism: | *E. coli*, ATCC 11229 | | |
| Dilution: | None | | |
| Neutralizer: | DE Neutralizer Broth | | |
| Numbers Control: | 100 × 10$^6$ | | |
| Bromadine 141 | 30 | 0 in 10$^6$ | 99.999+ |
|  | 60 | 0 in 10$^6$ | 99.999+ |
| Organism: | *Ps. aeruginosa*, ATCCF 15442 | | |
| Dilution: | None | | |
| Neutralizer: | DE Neutralizer | | |
| Numbers Control: | 100 × 10$^6$ | | |
| Bromadine 141 | 30 | 0 in 10$^6$ | 99.999+ |
|  | 60 | 0 in 10$^6$ | 99.999+ |
| Organism: | *E. coli*, ATCCF 11229 | | |
| Dilution: | None; 5% horse serum load incorporated into inoculum | | |
| Neutralizer: | DE Neutralizer Broth | | |
| Numbers Control: | 90 × 10$^6$ | | |
| Bromadine 141 | 30 | 0 in 10$^6$ | 99.999+ |
|  | 60 | 0 in 10$^6$ | 99.999+ |
| Organism: | *Ps. aeruginosa*, ATCC 15442 | | |
| Dilution: | None; 5% horse serum load incorporated into inoculum | | |
| Neutralizer: | DE Neutralizer Broth | | |
| Numbers Control: | 91 × 10$^6$ | | |
| Bromadine 141 | 30 | 0 in 10$^6$ | 99.999+ |
|  | 60 | 0 in 10$^6$ | 99.999+ |
| Organism: | *E. coli*, ATCC 11229 | | |
| Dilution: | 1:4 | | |
| Neutralizer: | DE Neutralizer Broth | | |
| Numbers Control: | 90 × 10$^6$ | | |
| Bromadine 141 | 30 | 0 in 10$^6$ | 99.999+ |
|  | 60 | 0 in 10$^6$ | 99.999+ |
| Organism: | *Ps. aeruginosa*, ATCC 15442 | | |
| Dilution: | 1:4 | | |
| Neutralizer: | DE Neutralizer Broth | | |
| Numbers Control: | 60 × 10$^6$ | | |
| Bromadine 141 | 30 | 0 in 10$^6$ | 99.999+ |
|  | 60 | 0 in 10$^6$ | 99.999+ |
| Organism: | *E. coli*, ATCC 11229 | | |
| Dilution: | 1:2 | | |
| Neutralizer: | DE Neutralizer Broth | | |
| Numbers Control: | 91 × 10$^6$ | | |
| Bromadine 141 | 30 | 0 in 10$^6$ | 99.999+ |
|  | 60 | 0 in 10$^6$ | 99.999+ |
| Organism: | *Ps. aeruginosa*, ATCC 15442 | | |
| Dilution: | 1:2 | | |
| Neutralizer: | DE Neutralizer | | |
| Numbers Control: | 90 × 10$^6$ | | |
| Bromadine 141 | 30 | 0 in 10$^6$ | 99.999+ |
|  | 60 | 0 in 10$^6$ | 99.999+ |

Procedure Reference:
AOAC, 13th Edition (1980)

In my prior patent application (Ser. No. 251,377, filed Apr. 6, 1981), I disclose bactericidal resins used for the disinfection of water wherein a strong base anion-exchange resin, usually of the type which contains quaternary ammonium groups, said resins being generally in the form of granules or beads, having anion-exchange sites, disposed or housed in a suitable container, for instance, a cylindrical tube having valved inlet and outlet openings, is contacted with an aqueous solution containing elemental iodine and water-soluble salts of iodine, such as potassium iodide, and potassium bromide. An illustrative composition, which is admixed with a cubic foot of the strong base anion-exchange resins, is an aqueous solution containing 200 g of iodine, 100 g of potassium iodide, 20 g of potassium bromide and 50 g of water. After admixing the said resin beads or granules with the aforesaid solution, the mixture is allowed to stand quiescently for about 16 to about 20 hours, and washing is then carried out with 4 to 5 gallons of deionized water. The result is to produce a body or bed of a bactericidal resin carrying a polyhalide complex of iodine and bromide ions. Such bactericidal resins are used for the disinfection of water by passing bacteria-contaminated water through a bed of said so-prepared bactericidal resins. The amounts of iodine and bromine released from the bactericidal resins when bacteria-contaminated water is passed therethrough are extremely low, being commonly of the order of about 0.2 to 0.4 mg/L. My present invention, as is evident from the foregoing description, is clearly distinguishable from the invention disclosed in my aforesaid co-pending application.

I claim:

1. A germicidal solution effective for surface disinfection which comprises a polyvinylpyrrolidone-aqueous solution of elemental iodine, a water-soluble iodide, and potassium bromide, said solution containing a high concentration of elemental iodine in solution.

2. The germicidal composition of claim 1, in which the water-soluble iodide is potassium iodide.

3. The germicidal composition of claim 2, in which the elemental iodine in solution in the composition is present in proportions in the range of about 1 to 5%.

4. The germicidal composition of claim 2, in which the polyvinylpyrrolidone is present in proportions in the range of about 2 to about 10%, by weight, of the germicidal solution.

5. The germicidal composition of claim 1, in which the polyvinylpyrrolidone is present in proportions of about 2 to about 10%, by weight, of the germicidal composition.

6. The germicidal composition of claim 5, in which the elemental iodine is present in proportions, by weight, substantially exceeding that of the water-soluble iodide, the water-soluble iodide is present in proportions, by weight, substantially exceeding that of the potassium bromide, and the elemental iodine is present in proportions exceeding the sum of the amounts of the water-soluble iodide and the potassium bromide.

7. The germicidal composition of claim 6, in which the water-soluble iodide is potassium iodide, and in which the ingredients are present in the ratios to each other represented by the following:
Elemental iodine: 200–230 g
Potassium iodide: 90–120 g
Potassium bromide: 10–30 g.

8. A germicidal solution effective for surface disinfection which comprises a polyvinylpyrrolidone-aqueous solution of elemental iodine, potassium iodide, and potassium bromide, in which the polyvinylpyrrolidone constitutes from about 2 to about 10%, by weight, of the solution; in which the elemental iodine, the potassium iodide and the potassium bromide are present in the ratios to each other represented by the following:
Elemental iodine: 200–230 g
Potassium iodide: 90–120 g
Potassium bromide 10–30 g;
in which the polyvinylpyrrolidone is present in proportions of about 2 to about 10%, and the elemental iodine is present in solution in proportions of about 1 to about 5%, said percentages of the polyvinylpyrrolidone and said elemental iodine being by weight of the solution.

9. A method of disinfecting solid surfaces contaminated with bacteria, microorganisms, protozoa, molds, viruses and other contaminants which are susceptible to destruction or inactivation by elemental iodine which comprises applying to such solid contaminated surfaces a polyvinylpyrrolidone-aqueous solution of elemental iodine, a water-soluble iodide, and potassium bromide, said elemental iodine being present in said solution in proportions effective to destroy or inactivate said surface contaminants.

10. The method of claim 9, in which the water-soluble iodide is potassium iodide.

11. The method of claim 9, in which the polyvinylpyrrolidone is present in proportions of about 2 to about 10%, by weight, of the germicidal composition.

12. The method of claim 11, in which the water-soluble iodide is potassium iodide, and in which the elemental iodine is present in proportions, by weight, substantially exceeding that of the water-soluble iodide, the water-soluble iodide is present in proportions, by weight, substantially exceeding that of the potassium bromide, and the elemental iodine is present in proportions exceeding the sum of the amounts of the water-soluble iodide and the potassium bromide.

13. The method of claim 12, in which the ingredients are present in the ratios to each other represented by the following:
Elemental iodine: 200–230 g
Potassium iodide: 90–120 g
Potassium bromide: 10–30 g.

14. The method of claim 9, in which the elemental iodine in solution in the composition is present in proportions in the range of about 1 to about 5% by weight of the solution.

15. The method of claim 9, in which the water-soluble iodide is potassium iodide, and in which the germicidal solution comprises a polyvinylpyrrolidone-aqueous solution of elemental iodine, potassium iodide, and potassium bromide, in which the polyvinylpyrrolidone constitutes from about 2 to about 10%, by weight, of the solution; in which the elemental iodine, the potassium iodide and the potassium bromide are present in the ratios to each other represented by the following:
Elemental iodine: 200–230 g
Potassium iodide: 90–120 g
Potassium bromide: 10–30 g;
in which the polyvinylpyrrolide is present in proportions of about 2 to about 10%, and the elemental iodine is present in solution in proportions of about 1 to about 5%, said percentages of the polyvinylpyrrolidone and said elemental iodine being by weight of the solution.

* * * * *